US005916773A

United States Patent [19]

Mele et al.

[11] Patent Number: 5,916,773

[45] Date of Patent: Jun. 29, 1999

[54] RECOMBINANT PRODUCTION OF FUSION PROTEINS COMPRISING ERYTHROPOIETIN AND GM-CSF COMPONENTS

[75] Inventors: Antonio Mele, Montecatini Terme; Rita De Santis, Pomezia; Cristina Carloni, Torvaianica; Annamaria Coscarella, Ardea, all of Italy

[73] Assignee: Menarini Ricerche S.p.A., Pomezia, Italy

[21] Appl. No.: 08/750,128

[22] PCT Filed: May 26, 1995

[86] PCT No.: PCT/EP95/02011

§ 371 Date: Nov. 27, 1996

§ 102(e) Date: Nov. 27, 1996

[87] PCT Pub. No.: WO95/33057

PCT Pub. Date: Dec. 7, 1995

[30] Foreign Application Priority Data

May 27, 1994 [IT] Italy .................................. FI94A0106

[51] Int. Cl.$^{6}$ .......................... C07K 19/00; C12N 15/62; A61K 38/19

[52] U.S. Cl. .................... 435/69.7; 435/69.5; 435/320.1; 435/325; 435/348; 435/419; 435/252.3; 435/254.11; 530/351; 536/23.4; 424/85.1; 514/2

[58] Field of Search ................................. 435/69.5, 69.7, 435/320.1, 325, 348, 419, 252.3, 254.11; 530/351, 350; 536/23.4; 424/85.1; 514/2

[56] References Cited

U.S. PATENT DOCUMENTS 5,567,611 10/1996 Ralph et al. ............................ 435/325

FOREIGN PATENT DOCUMENTS

95/11982 5/1995 WIPO .

OTHER PUBLICATIONS

Testa et al. "Cascade Transactivation of Growth Factor Receptors in Early Human Hematopoiesis" Mar. 15, 1993 pp. 1442–1456.

Clark et al. "The Human Hematopoietic Colony–Stimulating Factors" Jun. 5, 1987, pp. 1229–1237.

Valtieri et al. "Erythropoietin Alone Induces Erythroid Burst Formation by Human Embryonic but Not Adult BFU–E in Unicellular Serum–Free Culture" Jul. 1989 pp. 460–470.

Felgner "Cationic Liposome–Mediated Transfection" pp. 21–37.

Urlaub et al. "Isolation of Chinese Hamster Cell Mutants Deficient in Dihydrofolate Reductase Activity" Jul. 1980 pp. 4216–4221.

C. Peschle "Stringently Purified Human Hematopoietic Progenitors/Stem Cells: Analysis of Cellular/Molecular Mechanisms Underlying Early Hematopoiesis" Apr. 12, 1993, pp. 356–370.

Weich, N.S., et al. (1993) *Exp. Hematol.* 21: 647–55.

*Primary Examiner*—David L. Fitzgerald
*Attorney, Agent, or Firm*—Lowe, Price, LeBlanc & Becker

[57] ABSTRACT

It is described a hybrid molecule of formula GM-CSF-L-EPO or EPO-L-GM-CSF useful for the stimulation of hematopoiesis, comprising GM-CSF and EPO molecules fused together by means of a linker L having a variable length of amino acids, GM-CSF and EPO molecules being either complete molecules or fragments thereof. Such hybrid molecules exhibit a higher specifity of action on erythroid differentiation if compared to that of an equimolar mixture of not-linked GM-CSF and EPO molecules. Further, the present invention describes: DNA sequences encoding such hybrid molecules, which stimolate the hematopoiesis; plasmid vectors containing the genes encoding hybrid molecules and directing their synthesis in host cells; the use of such hybrid molecules for the preparation of a pharmaceutical composition and such pharmaceutical composition useful for stimolation of hematopoiesis.

21 Claims, 5 Drawing Sheets

GM-CSF-L1(Δ1-4)EPO (MEN11301)

GM-CSF-L 21(Δ1-4)EPO (MEN11300)

EPO-L3-GM-CSF (MEN11303)

RIDUCTION OF LINKERS L1 TO L2 BY MEANS OF RESTRICTION WITH NaeI

NaeI NaeI

5'GCC|GGCGGAGGAGGTTCCGGAGGAGCC|GGCTCGGGGGGCGGCGGCTCA3'

Ala Gly Gly Gly Gly Ser Gly Gly Ala Gly Ser Gly Gly Gly Gly Ser

NaeI

5'GCC|GGCTCGGGGGGCGGCGGCTCA3'

Ala Gly Ser Gly Gly Gly Gly Ser

Figure 3

SEQUENCE LISTING

```
(1) GENERAL INFORMATION:

   (iii) NUMBER OF SEQUENCES: 12


(2) INFORMATION FOR SEQ ID NO: 1:

     (i) SEQUENCE CHARACTERISTICS:
          (A) LENGTH: 105 base pairs
          (B) TYPE: nucleic acid
          (C) STRANDEDNESS: single
          (D) TOPOLOGY: linear

    (ii) MOLECULE TYPE: cDNA

   (iii) HYPOTHETICAL: NO

    (xi) SEQUENCE DESCRIPTION: SEQ ID NO: 1:

ACCCTCGGTC AGGTCCTCCG GCCGCCTCCT CCAAGGCCTC CTCGGCCGAG CCCCCCGCCG       60

CCGAGTGAGT AGACACTGTC GGCTCAGGAC CTCTCCATGG AGAAC                      105


(2) INFORMATION FOR SEQ ID NO: 2:

     (i) SEQUENCE CHARACTERISTICS:
          (A) LENGTH: 48 base pairs
          (B) TYPE: nucleic acid
          (C) STRANDEDNESS: single
          (D) TOPOLOGY: linear

    (ii) MOLECULE TYPE: cDNA

   (iii) HYPOTHETICAL: NO

    (xi) SEQUENCE DESCRIPTION: SEQ ID NO: 2:

GCCGGCGGAG GAGGTTCCGG AGGAGCCGGC TCGGGGGGCG GCGGCTCA                    48


(2) INFORMATION FOR SEQ ID NO: 3:

     (i) SEQUENCE CHARACTERISTICS:
          (A) LENGTH: 16 amino acids
          (B) TYPE: amino acid
          (C) STRANDEDNESS: single
          (D) TOPOLOGY: linear

    (ii) MOLECULE TYPE: peptide

   (iii) HYPOTHETICAL: NO
```

(xi) SEQUENCE DESCRIPTION: SEQ ID NO: 3:

```
Ala Gly Gly Gly Gly Ser Gly Gly Ala Gly Ser Gly Gly Gly Gly Ser
1               5                   10                  15
```

(2) INFORMATION FOR SEQ ID NO: 4:

(i) SEQUENCE CHARACTERISTICS:
(A) LENGTH: 969 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO: 4:

```
ATGTGGCTGC AGAGCCTGCT GCTCTTGGGC ACTGTGGCCT GCAGCATCTC TGCACCCGCC     60

CGCTCGCCCA GCCCCAGCAC GCAGCCCTGG GAGCATGTGA ATGCCATCCA GGAGGCCCGG    120

CGTCTCCTGA ACCTGAGTAG AGACACTGCT GCTGAGATGA ATGAAACAGT AGAAGTCATC    180

TCAGAAATGT TTGACCTCCA GGAGCCGACC TGCCTACAGA CCCGCCTGGA GCTGTACAAG    240

CAGGGCCTGC GGGGCAGCCT CACCAAGCTC AAGGGCCCCT TGACCATGAT GGCCAGCCAC    300

TACAAGCAGC ACTGCCCTCC AACCCCGGAA ACTTCCTGTG CAACCCAGCA TATCACCTTT    360

GAAAGTTTCA AAGAGAACCT GAAGGACTTT CTGCTTGTCA TCCCCTTTGA CTGCTGGGAG    420

CCAGTCCAGG AGGCCGGCGG AGGAGGTTCC GGAGGAGCCG GCTCGGGGGG CGGCGGCTCA    480

CTCATCTGTG ACAGCCGAGT CCTGGAGAGG TACCTCTTGG AGGCCAAGGA GGCCGAGAAT    540

ATCACGACGG GCTGTGCTGA ACACTGCAGC TTGAATGAGA ATATCACTGT CCCAGACACC    600

AAAGTTAATT TCTATGCCTG GAAGAGGATG GAGGTCGGGC AGCAGGCCGT AGAAGTCTGG    660

CAGGGCCTGG CCCTGCTGTC GGAAGCTGTC CTGCGGGGCC AGGCCCTGTT GGTCAACTCT    720

TCCCAGCCGT GGGAGCCCCT GCAGCTGCAT GTGGATAAAG CCGTCAGTGG CCTTCGCAGC    780

CTCACCACTC TGCTTCGGGC TCTGGGAGCC CAGAAGGAAG CCATCTCCCC TCCAGATGCG    840

GCCTCAGCTG CTCCACTCCG AACAATCACT GCTGACACTT TCCGCAAACT CTTCCGAGTC    900

TACTCCAATT TCCTCCGGGG AAAGCTGAAG CTGTACACAG GGGAGGCCTG CAGGACAGGG    960

GACAGATGA                                                            969
```

(2) INFORMATION FOR SEQ ID NO: 5:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO: 5:

```
GCCGGCTCGG GGGGCGGCGG CTCA                                            24
```

(2) INFORMATION FOR SEQ ID NO: 6:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (iii) HYPOTHETICAL: NO (xi) SEQUENCE DESCRIPTION: SEQ ID NO: 6:

```
Ala Gly Ser Gly Gly Gly Gly Ser
1               5
```

(2) INFORMATION FOR SEQ ID NO: 7:

(i) SEQUENCE CHARACTERISTICS:
(A) LENGTH: 945 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO: 7:

```
ATGTGGCTGC AGAGCCTGCT GCTCTTGGGC ACTGTGGCCT GCAGCATCTC TGCACCCGCC     60

CGCTCGCCCA GCCCCAGCAC GCAGCCCTGG GAGCATGTGA ATGCCATCCA GGAGGCCCGG    120

CGTCTCCTGA ACCTGAGTAG AGACACTGCT GCTGAGATGA ATGAAACAGT AGAAGTCATC    180

TCAGAAATGT TTGACCTCCA GGAGCCGACC TGCCTACAGA CCCGCCTGGA GCTGTACAAG    240

CAGGGCCTGC GGGGCAGCCT CACCAAGCTC AAGGGCCCCT TGACCATGAT GGCCAGCCAC    300

TACAAGCAGC ACTGCCCTCC AACCCCGGAA ACTTCCTGTG CAACCCAGAC TATCACCTTT    360

GAAAGTTTCA AAGAGAACCT GAAGGACTTT CTGCTTGTCA TCCCCTTTGA CTGCTGGGAG    420

CCAGTCCAGG AGGCCGGCTC GGGGGGCGGC GGCTCACTCA TCTGTGACAG CCGAGTCCTG    480

GAGAGGTACC TCTTGGAGGC CAAGGAGGCC GAGAATATCA CGACGGGCTG TGCTGAACAC    540

TGCAGCTTGA ATGAGAATAT CACTGTCCCA GACACCAAAG TTAATTTCTA TGCCTGGAAG    600

AGGATGGAGG TCGGGCAGCA GGCCGTAGAA GTCTGGCAGG GCCTGGCCCT GCTGTCGGAA    660

GCTGTCCTGC GGGGCCAGGC CCTGTTGGTC AACTCTTCCC AGCCGTGGGA GCCCCTGCAG    720

CTGCATGTGG ATAAAGCCGT CAGTGGCCTT CGCAGCCTCA CCACTCTGCT TCGGGCTCTG    780

GGAGCCCAGA AGGAAGCCAT CTCCCCTCCA GATGCGGCCT CAGCTGCTCC ACTCCGAACA    840

ATCACTGCTG ACACTTTCCG CAAACTCTTC CGAGTCTACT CCAATTTCCT CCGGGGAAAG    900

CTGAAGCTGT ACACAGGGGA GGCCTGCAGG ACAGGGGACA GATGA                    945
```

(2) INFORMATION FOR SEQ ID NO: 8:

(i) SEQUENCE CHARACTERISTICS:
(A) LENGTH: 48 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO: 8:

```
GCCGGCGGAG GAGGCTCGGG AGGAGGAGGT TCCGGAGGAG CCGGCTCA                  48
```

(2) INFORMATION FOR SEQ ID NO: 9:

(i) SEQUENCE CHARACTERISTICS:
(A) LENGTH: 16 amino acids
(B) TYPE: amino acid (C) STRANDEDNESS: single
(D) TOPOLOGY: linear (ii) MOLECULE TYPE: peptide (iii) HYPOTHETICAL: NO (xi) SEQUENCE DESCRIPTION: SEQ ID NO: 9:

```
Ala Gly Gly Gly Gly Ser Gly Gly Gly Gly Ser Gly Gly Ala Gly Ser
1               5                   10                  15
```

(2) INFORMATION FOR SEQ ID NO: 10:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO: 10:

```
TCCTCCCGAG CCTCCTCCGC CGGCTCTGTC CCCTGT                                36
```

(2) INFORMATION FOR SEQ ID NO: 11:

(i) SEQUENCE CHARACTERISTICS:
(A) LENGTH: 57 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO: 11:

```
GGAGGAGGCT CGGGAGGAGG AGGTTCCGGA GGAGCCGGCT CAGCACCCGC CCGCTCG         57
```

(2) INFORMATION FOR SEQ ID NO: 12:

(i) SEQUENCE CHARACTERISTICS:
(A) LENGTH: 1011 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO: 12:

```
ATGGGGGTGC ACGAATGTCC TGCCTGGCTG TGGCTTCTCC TGTCCCTGCT GTCGCTCCCT      60

CTGGGCCTCC CAGTCCTGGG CGCCCCACCA CGCCTCATCT GTGACAGCCG AGTCCTGGAG     120

AGGTACCTCT TGGAGGCCAA GGAGGCCGAG AATATCACGA CGGGCTGTGC TGAACACTGC     180

AGCTTGAATG AGAATATCAC TGTCCCAGAC ACCAAAGTTA ATTTCTATGC CTGGAAGAGG     240

ATGGAGGTCG GGCAGCAGGC CGTAGAAGTC TGGCAGGGCC TGGCCCTGCT GTCGGAAGCT     300

GTCCTGCGGG GCCAGGCCCT GTTGGTCAAC TCTTCCCAGC CGTGGGAGCC CCTGCAGCTG     360

CATGTGGATA AAGCCGTCAG TGGCCTTCGC AGCCTCACCA CTCTGCTTCG GGCTCTGGGA     420

GCCCAGAAGG AAGCCATCTC CCCTCCAGAT GCGGCCTCAG CTGCTCCACT CCGAACAATC     480

ACTGCTGACA CTTTCCGCAA ACTCTTCCGA GTCTACTCCA ATTTCCTCCG GGGAAAGCTG     540

AAGCTGTACA CAGGGGAGGC CTGCAGGACA GGGGACAGAG CCGGCGGAGG AGGCTCGGGA     600
```

-continued

```
GGAGGAGGTT CCGGAGGAGC CGGCTCAGCA CCCGCCCGCT CGCCCAGCCC CAGCACGCAG    660

CCCTGGGAGC ATGTGAATGC CATCCAGGAG GCCCGGCGTC TCCTGAACCT GAGTAGAGAC    720

ACTGCTGCTG AGATGAATGA AACAGTAGAA GTCATCTCAG AAATGTTTGA CCTCCAGGAG    780

CCGACCTGCC TACAGACCCG CCTGGAGCTG TACAAGCAGG GCCTGCGGGG CAGCCTCACC    840

AAGCTCAAGG GCCCCTTGAC CATGATGGCC AGCCACTACA AGCAGCACTG CCCTCCAACC    900

CCGGAAACTT CCTGTGCAAC CCAGACTATC ACCTTTGAAA GTTTCAAAGA GAACCTGAAG    960

GACTTTCTGC TTGTCATCCC CTTTGACTGC TGGGAGCCAG TCCAGGAGTG A            1011
```

RECOMBINANT PRODUCTION OF FUSION PROTEINS COMPRISING ERYTHROPOIETIN AND GM-CSF COMPONENTS

This is a continuation-in-part of International Application PCT/EP95/02011 having an international filing date of May 26, 1995.

FIELD OF THE INVENTION

The present invention relates to hybrid hematopoietic factors for the stimulation of hematopoiesis. In particular, to hybrid molecules of formula GM-CSF-L-EPO or EPO-L-GM-CSF comprising complete GM-CSF and EPO molecules or fragments thereof fused by means of a linking peptide (hereinafter simply indicated by the definition linker) L having a variable length in amino acids. Such hybrid molecules exhibit a higher specificity of action on erythroid differentiation if compared to that of an equimolar mixture of not-linked GM-CSF and EPO molecules.

STATE OF THE ART

Hematopoiesis is a multi-step cell proliferation and differentiation process starting from a pool of multipotent stem cells. These cells can proliferate and differenziate into hematopoietic progenitors in reply to different stimuli.

A group of proteins named growth factors or Colony Stimulating Factors (CSFs) or cytokines control survival, proliferation and differentiation of stem and progenitor cells. Furthermore, they affect several functional activities of mature terminal cells. In brief, at the level of immature cells, CSFs assure the self-renewal of the staminal pool and activate the first stage of hematopoietic differentiation; in the middle stage, when cell proliferation is associated to a progressive acquisition of characteristics of mature cells, they enormously enhance the number of differentiating cells; in the terminal stage they control the circulation and the activation of mature cells.

For many CSFs, the target cell is known. Interleukin 3 (IL3) acts on multipotent (CFU-GEMM), myeloid (CFU-GM), erythroid (BFU-E) and megakaryocytic (CFU-MK) progenitors, whereas GM-CSF exerts its effects on early progenitors. Erythropoietin (EPO), G-CSF, interleukin 5 (IL5) and M-CSF are specific for end-stage progenitors of the erythroid (CFU-E), granulocytic (CFU-G), eosinophilic (CFU-Eo) and monocytic (CFU-M) lineage, respectively. The importance of these molecules is justified by their potential clinical use.

In particular, the EPO administration, which causes an increase of blood cells, is useful in case of anaemia, aplasia or marrow hypoplasia induced by chemotherapy or radiant theraphy and in hemodialysed patients with chronic renal failure.

The administration of GM-CSF, as shown by some preliminary clinical studies, is useful when the organism absolutely needs to produce granulocytes, for example under AIDS conditions or during anti-blastic theraphy in case of neoplasia or transplantation. The interaction of several growth factors at the level of single cells can have sinergetic or antagonist additive effects. For example, severe anemia responds well to the combination of GM-CSF and IL3 with EPO (Clark S. C., Kamen R., 1987, Science, 236:1229).

Since current blood available is not sufficient for covering transfusion needs and as the risk of haematic contact diseases like AIDS, B and C hepatitis, etc. is higher and higher, it is justified the industrial interest for the production of recombinant hematopoietic factors or new molecules with hemopoietic activity.

Patent application WO 92/06116 discloses recombinant hematopoietic hybrid growth factors comprising an early factor and a late factor. As early factors are disclosed IL-3 and GM-CSF, whilst as late factors it discloses EPO, G-CSF, IL5 and M-CSF. Said patent application describes only hybrid growth factors IL3:EPO, EPO:IL3 and IL3:G-CSF, wherein the two components of each hybrid factor can be fused together directly or by means of a linker.

Although said patent application also quotes the GM-CSF molecule (pag.7), no description or indication is given with reference to the behaviour and use of said molecule in combination with EPO.

The authors of patent application WO 92/06116 assume that the early factor (IL3) down-regulates the expression of the receptors for the late fator (EPO) and therefore it leads to decrease the receptors for the late factor. On the other hand, Testa U., et al. (Blood, 81, 1442–1456, 1993) found that the early factor acts positively up-stimulating the expression of receptors for late factors. Therefore, one come to the conclusion that the effects induced by early/late factors have not been understood yet.

Further, the authors of said patent application have disclosed data on the biological activity of the hybrid factor IL3:EPO or EPO:IL3 (clonogenic test; Table IV) showing that said hybrid molecules stimulate BFU-E and CFU-E colonies of bone marrow cells. As they did not report data on the induction of CFU-GM colonies, it was not possible to foresee or argue a specificity of action on the erythroid differentiation by means of said hybrid factors. Moreover, said Table IV did not show substantial differences between the effect of the IL3:EPO or EPO:IL3 hybrid factors on the production of erythroid cells (BFU-E and CFU-E cells) and the effect exerted by IL3+EPO mixture. Furthermore, the clonogenic test reported in said application was performed with not-purified progenitor cells of bone marrow; it is therefore possible that the final observation was conditionated by the presence of contaminants or secondary cells (that is cells secreting endogenous growth factors; Peschle C. et al., 1993, Stem Cell, 11, 356–370).

In short, in the light of publications cited, we can consider that the data disclosed in WO 92/06116 are at present hardly interpretable.

SUMMARY OF THE INVENTION

The authors of the present invention found that the new hybrid molecules of formula GM-CSF-L-EPO or EPO-L-GM-CSF comprising complete GM-CSF and EPO molecules or fragments thereof fused by means of a linker L having a variable length of amino acids surprisingly exhibit a higher specificity of action on erythroid differentiation if compared to that of an equimolar mixture of not-linked GM-CSF and EPO molecules. It was not possible to assume or foresee this result on the basis of the state of the art.

Furthermore, the present invention relates to a nucleotide sequence encoding said fused molecule, to an expression vector comprising said nucleotide sequence and to a cell host comprising said vector. The present invention also relates to the use of said fused molecules for the preparation of a pharmaceutical composition and to said pharmaceutical composition useful for the stimulation of hematopoiesis.

BRIEF DESCRIPTION OF FIGURES AND SEQUENCES

FIGS. 1A–1C show the structural scheme referring to hybrid molecules GM-CSF-L1-(Δ1-4)EPO, GM-CSF-L2-

(Δ1-4)EPO and EPO-L3-GM-CSF wherein L1 and L3 are the linkers of a sequence of 16 amino acids whilst L2 is a linker of 8 amino acids. The sign (Δ1-4)EPO indicates that the EPO molecule lacks the first four amino acids.

FIG. 3 shows the riduction of linker L1 (16aa) to L2 (8aa) by means of restriction endonuclease digestion of DNA with NaeI.

SEQ ID NQ:1 reports the sequence of oligonucleotide of 105 bases.

SEQ ID NO:2 reports the nucleotide sequence of 48 bases encoding the linker L1.

SEQ ID NO:3 reports the sequence of 16 amino acids of the linker L1.

SEQ ID NO:4 reports the nucleotide sequence of the hybrid molecule GM-CSF-L1-(Δ1-4)EPO.

SEQ ID NO:5 reports the nucleotide sequence of 24 bases encoding the linker L2.

SEQ ID NO:6 reports the sequence of 8 amino acids of the linker L2.

SEQ ID NO:7 reports the nucleotide sequence of the hybrid molecule GM-CSF-L2-(Δ1-4)EPO.

SEQ ID NO:8 reports the nucleotide sequence of 48 bases encoding the linker L3.

SEQ ID NO:9 reports the sequence of 16 amino acids of the linker L3.

SEQ ID NO:10 reports the nucleotide sequence of an oligonucleotide of 36 bases.

SEQ ID NO:11 reports the nucleotide sequences of an oligonucleotide of 57 bases.

SEQ ID NO:12 reports the nucleotide sequence of the hybrid molecule EPO-L3-GM-CSF.

DETAILED DESCRIPTION OF THE INVENTION

According to the present invention, authors obtained many hybrid molecules by means of fusion of genic fragments encoding GM-CSF, linker and EPO, and their expression in host cells. Host cells were selected from the group consisting of bacterial, yeast, insect, plant or mammalian cells. The use of CHO cells is preferable.

The hybrid molecules according to the invention are indicated by the formula GM-CSF-L-EPO or EPO-L-GM-CSF, wherein said hybrid molecule is constituted by complete molecules of GM-CSF (127 amino acids) and EPO (166 amino acids) or by fragments thereof fused by means of a linker L having a variable length in amino acids.

Preferably the above said linker L is constituted of 5–50 amino acids and contains at least one sequence GlyGlyXGlySer wherein X can be Gly or Ala.

The construction of hybrid genes encoding the proteins according to the invention is as follows.

I) A sequence of DNA encoding the fusion protein comprising the GM-CSF at the N-terminus, the linker and the EPO at the C-terminus, that is comprising from 5' to 3' the following portions:

a) the untranslated 5' region of cDNA of GM-CSF;

b) the GM-CSF encoding sequence;

c) an oligonucleotide encoding the linker;

d) the EPO encoding sequence;

e) the untranslated region of EPO.

II) A sequence of DNA encoding the fusion protein comprising the EPO at the N-terminus, the linker and the GM-CSF at the C-terminus, that is comprising from 5' to 3' the following portions:

a) the untranslated 5' region of cDNA of EPO;

b) the EPO encoding sequence;

c) an oligonucleotide encoding the linker;

d) the GM-CSF encoding sequence;

e) the untranslated region of GM-CSF.

Figure 1A:
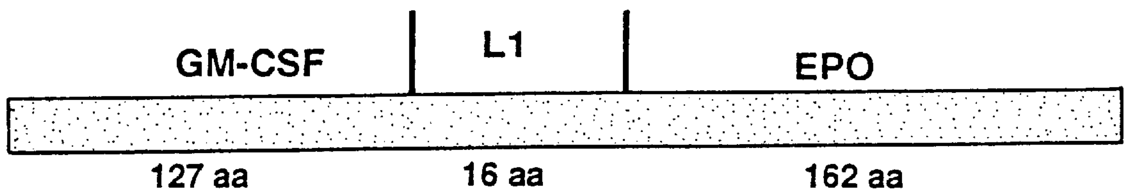
Figure 1B:
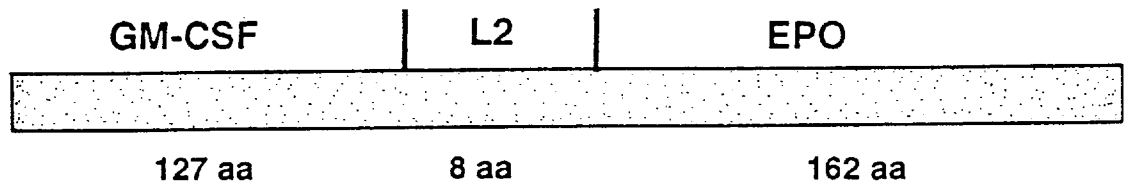
Figure 1C:
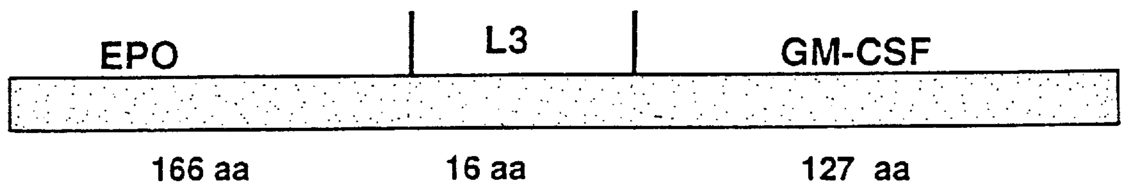

According to a preferred embodiment of the invention, the hybrid molecules obtained are the following:

GM-CSF-L1-(Δ1-4)EPO (also named MEN 11301), GM-CSF-L2-(Δ1-4)EPO (also named MEN 11300) and EPO-L3-GM-CSF (also named MEN 11303), wherein L1 and L3 refer to a linker of 16 amino acids of length, whilst L2 refers to a linker of 8 amino acids of length. The term (Δ1-4)EPO means that the EPO molecule lacks the first four amino acids and it is also indicated as 5–166 amino acids (5–166 aa) of EPO. The structural schemes according to the above molecules are shown in FIGS. 1A–C.

According to this embodiment, the above hybrid genes were cloned in expression vectors according to the patent application WO9511982 and transfected in CHO cells. The recombinant hybrid cells expressed in CHO cells were functionally studied by a clonogenic test on human purified stem cells. The obtained functional data show that the three hybrid molecules, released in the media by transfectants, induce erythroid differentiation. Surprisingly, the ratio of the number of erythroid colonies and granulocyte-macrophage colonies in cultures treated with the hybrid molecules of the invention is higher than in the cultures treated with the mixture of the two factors GM-CSF and EPO, indicating a functional advantage in the selective induction of the erythroid differentiation of the molecules fused in a single polipeptide chain if compared to the mixture (Table 1).

Some specific embodiments according to the present invention are hereinafter described in the following examples.

EXAMPLE 1

Construction of the hybrid gene encoding the fusion protein GM-CSF-L1-(Δ1-4) EPO The hybrid gene encoding the fusion protein comprising GM-CSF at the N-terminus, the linker L1 and EPO at the C-terminus, was obtained as follows.

A) The EPO cDNA inserted in pGEM7Z (5' SmaI-3'EcoRI) (Promega Biotec, Madison, Wis., USA) was cloned in the KpnI-EcoRI sites of the pGEM4Z vector (Promega Biotec, Madison, Wis., USA). The restriction with KpnI implies the elimination of the first 17 amino acids of the protein; amino acids from +5 to +17 were then restored by means of the fusion with the linker sequence, as better specified in B).

B) The cDNA portion of GM-CSF used for the construction of the fusion protein was obtained by means of PCR using as template the cDNA of the GM-CSF cloned in pGEM7Z (5'EcoRI-3'HindIII) and as 5' primer the oligonucleotide corresponding to the T7 promoter of the pGEM7Z vector (Promega Biotec, Madison, Wis.,USA) and as 3' primer the oligonucleotide of 105 bases, whose sequence is reported in SEQ ID NO:1 having 18 bases complementary to the 3' coding region of GM-CSF (with exclusion of the stop codon), 48 bases (whose sequence is reported in SEQ ID NO:2 and in FIG. 3) encoding a molecular linker whose sequence is a modified version of the linker described by Huston et al., (PNAS, 1988, USA, 85:5879–5883) and 39 bases encoding the amino acids from position +5 to position +17 of EPO.

Figure 2:
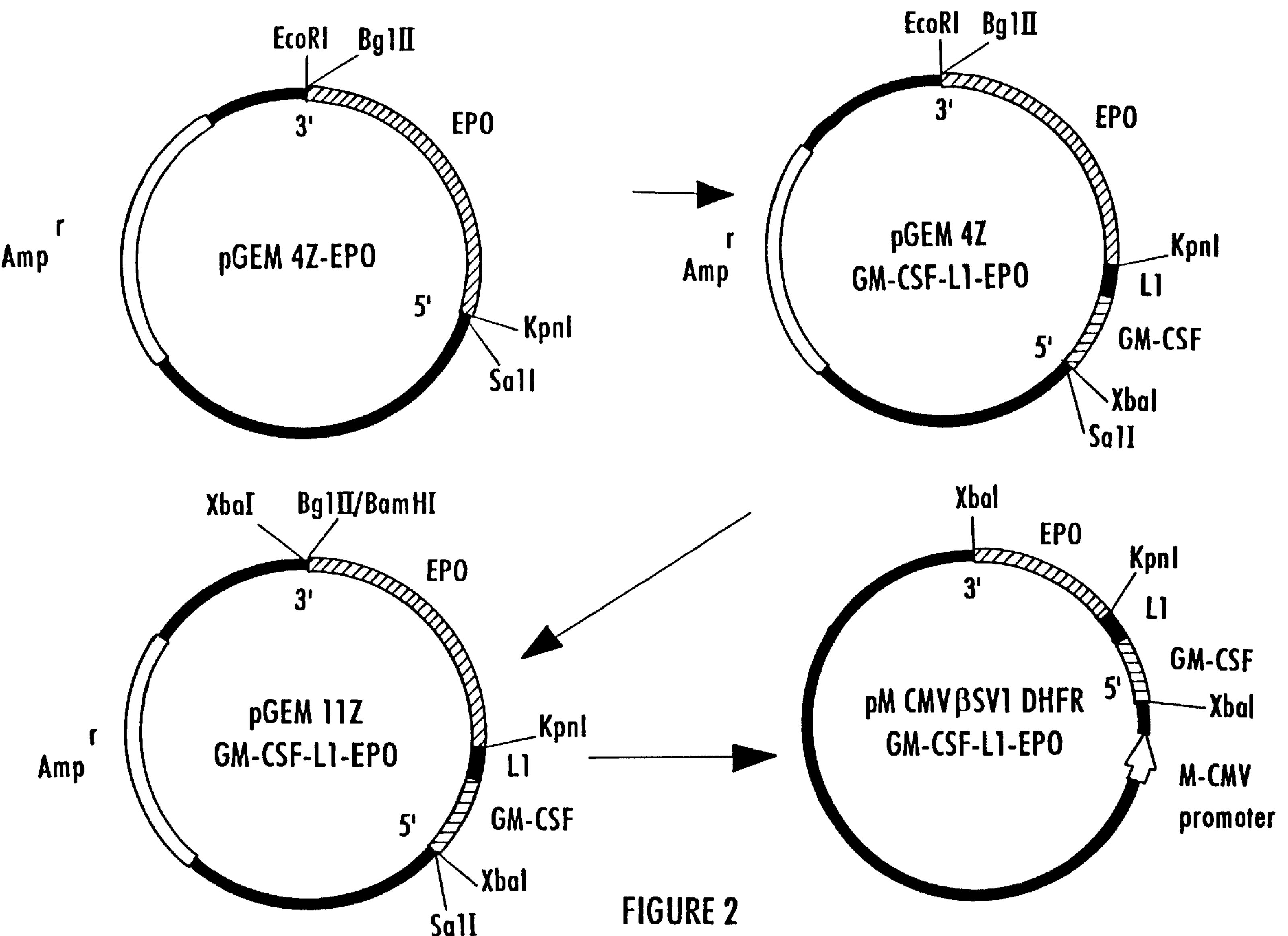
FIG. 2 shows the construction of the hybrid gene encoding the fusion hybrid protein GM-CSF-L1-(Δ1-4)EPO.

The PCR product was cleaved at XbaI-KpnI. This digestion implies the elimination at 3' of the last 6 nucleotides encoding amino acids +16 and +17 of EPO, already present in the EPO sequence cloned in pGEM4Z-EPO. The digested amplified product was cloned in the same sites of the pGEM4Z-EPO above described, restoring the EPO amino acids at position from +5 to +15. The pGEM4Z-GM-CSF-L1-EPO was digested with SalI/BglII and the fragment cloned in pGEM11Z (Promega Biotec) in the sites SalI e BamHI and therefore in the final vector pMCMVβSV1DHFR (already described in patent application WO9511982), cloning in the XbaI site (FIG. 2).

The nucleotide sequence encoding the hybrid molecule GM-CSF-L1-(Δ1-4)EPO determined with the method of Sanger (SEQUENASE Version 2.0 DNA Sequencing kit. UNITED STATES BIOCHEMICAL) is reported in SEQ ID NO:4.

The amino acid sequence of the mature hybrid protein GM-CSF-L1-(Δ1-4) comprises:

a) 127 amino acids of GM-CSF;

b) a linker of 16 amino acids having the sequence: AlaGlyGlyGlyGlySerGlyGlyAla-GlySerGlyGlyGlyGlySer (SEQ ID NO:3 and FIG. 3);

c) 162 amino acids of EPO.

EXAMPLE 2

Construction of the hybrid gene encoding the fusion protein GM-CSF-L2-(Δ1-4)EPO

The hybrid gene encoding the fusion protein comprising GM-CSF at the N-terminus, the linker L2 (24 bases reported in SEQ ID NO:5 and in FIG. 3) and EPO at the C-terminus, was obtained as follows.

A) The pGEM4Z-GM-CSF-L1-EPO construct was digested with the restriction enzyme NaeI. This enzyme has two restriction sites in the linker L1. The digestion with NaeI eliminates 24 bases of the linker L1 leaving, between GM-CSF and EPO, the amino acid sequence AlaGlySer-GlyGlyGlyGlySer (SEQ ID NO:6 and FIG. 3).

Subcloning steps for transferring GM-CSF-L2-(Δ1-4) EPO from pGEM4Z to pMCMVβSV1DHFR are analogous to those described for GM-CSF-L1-(Δ1-4)EPO (FIG. 2).

The nucleotide sequence encoding the hybrid molecule GM-CSF-L2-(Δ1-4)EPO determined with the method of Sanger (SEQUENASE Version 2.0 DNA Sequencing kit. UNITED STATES BIOCHEMICAL) is reported in SEQ ID NO:7.

The amino acid sequence of the mature hybrid protein GM-CSF-L2-(Δ1-4)EPO comprises:

a) 127 amino acids of GM-CSF;

b) a linker of 8 amino acids having the sequence AlaGly-SerGlyGlyGlyGlySer (SEQ ID NO:6);

c) 162 amino acids of EPO.

EXAMPLE 3

Construction of the hybrid gene encoding the fusion protein EPO-L3-GM-CSF

The cDNA encoding the fusion protein comprising EPO at the N-terminus, the linker L3 (a sequence of 16 amino acids reported in SEQ ID NO:9) and GM-CSF at the C-terminus, was prepared as follows.

A) EPO cDNA was amplified using as template pGEM7Z-EPO after EcoRI restriction emzyme digestion, as 5' primer the oligonucleotide corresponding to the SP6 promoter (Promega, Biotec, Madison, Wis., USA) and as 3' primer an oligonucleotide of 36 bases (SEQ ID NO:10), wherein 12 bases were complementary to the 3' of the template (excluding the stop codon) and 24 bases encoded the 5' portion of the linker L3;

B) GM-CSF cDNA was amplified using as template pGEM7Z-GM-CSF after EcoRI restriction enzyme digestion, as 3' primer the SP6 and as 5' primer an oligonucleotide of 57 bases (SEQ ID NO:11), wherein 42 bases encoded the 3' portion of the linker L3 and 15 bases were complementary to the sequence encoding the first 5 amino acids of the mature protein.

Figure 4:
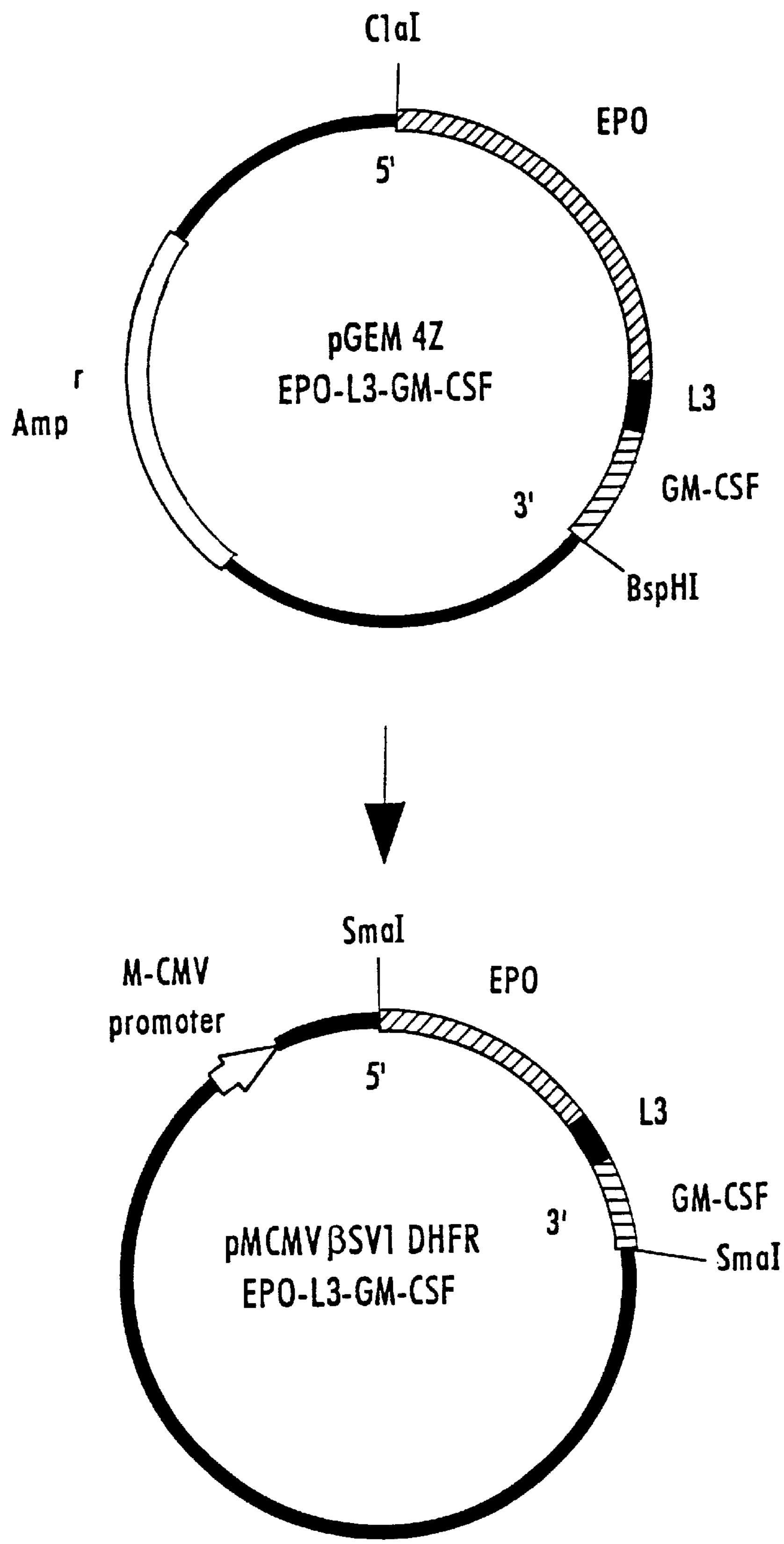
FIG. 4 shows the construction of the hybrid gene encoding the fusion hybrid protein EPO-L3-GM-CSF.

The complete nucleotide sequence of linker L3 is reported in SEQ ID NO:8. The products of the two PCRs, digested respectively with SacI/AvaI and AvaI/BamHI enzymes, were cloned in pGEM4Z in the restriction sites SacI/BamHI. The pGEM4Z-EPO-L3-GM-CSF was digested at ClaI/BspHI and, after filling in ends to have them blunt by means of the KLENOW polymerase (BOEHRINGER MANNHEIM), the fragment was cloned in the SmaI site of pMCMVβSV1DHFR (FIG. 4).

The nucleotide sequence encoding the hybrid molecule EPO-L3-GM-CSF determined with the method of Sanger (as above) is reported in SEQ ID NO:12.

The amino acid sequence of the mature hybrid protein EPO-L3-GM-CSF comprises:

a) 166 amino acids of EPO;

b) a linker of 16 amino acids having the sequence: AlaGlyGlyGlyGlySerGlyGlyG-lyGlySerGlyGlyAlaGlySer (SEQ ID NO:9);

c) 127 amino acids of GM-CSF.

Preparation of the cell lines producing the recombinant hybrid molecules GM-CSF-L1-(Δ1-4)EPO, GM-CSF-L2-(Δ1-4)EPO and EPO-L3-GM-CSF The mammalian cells used for the expression of the recombinant hybrid molecules are CHOdhfr$^-$ (CHO DUKXB1)(Urlaub G., Chaisin L. A., 1980, Proc. Natl. Acad. Sci. 77:4216).

The cells were transfected using the LIPOFECTIN produced by GIBCO BRL (Felgner P. L., Holm M., 1989, Focus, 11–2:21). The clones, selected after transfection, were subjected to amplification cicles upon increasing concentrations of methotrexate (SIGMA).

Determination of the expression levels

The fusion proteins were assayed in the conditioned medium by two ELISA tests: i) EPO ELISA (BOEHRINGER MANNHEIM); ii) GM-CSF ELISA (AMERSHAM).

Biological characterization

The evaluation of the biological activity of the hybrid proteins produced in the conditioned media was obtained by clonogenic test on human stem cells as known in the state of the art (Valtieri M., et al., 1989, Blood, 74:460).

Figure 5:
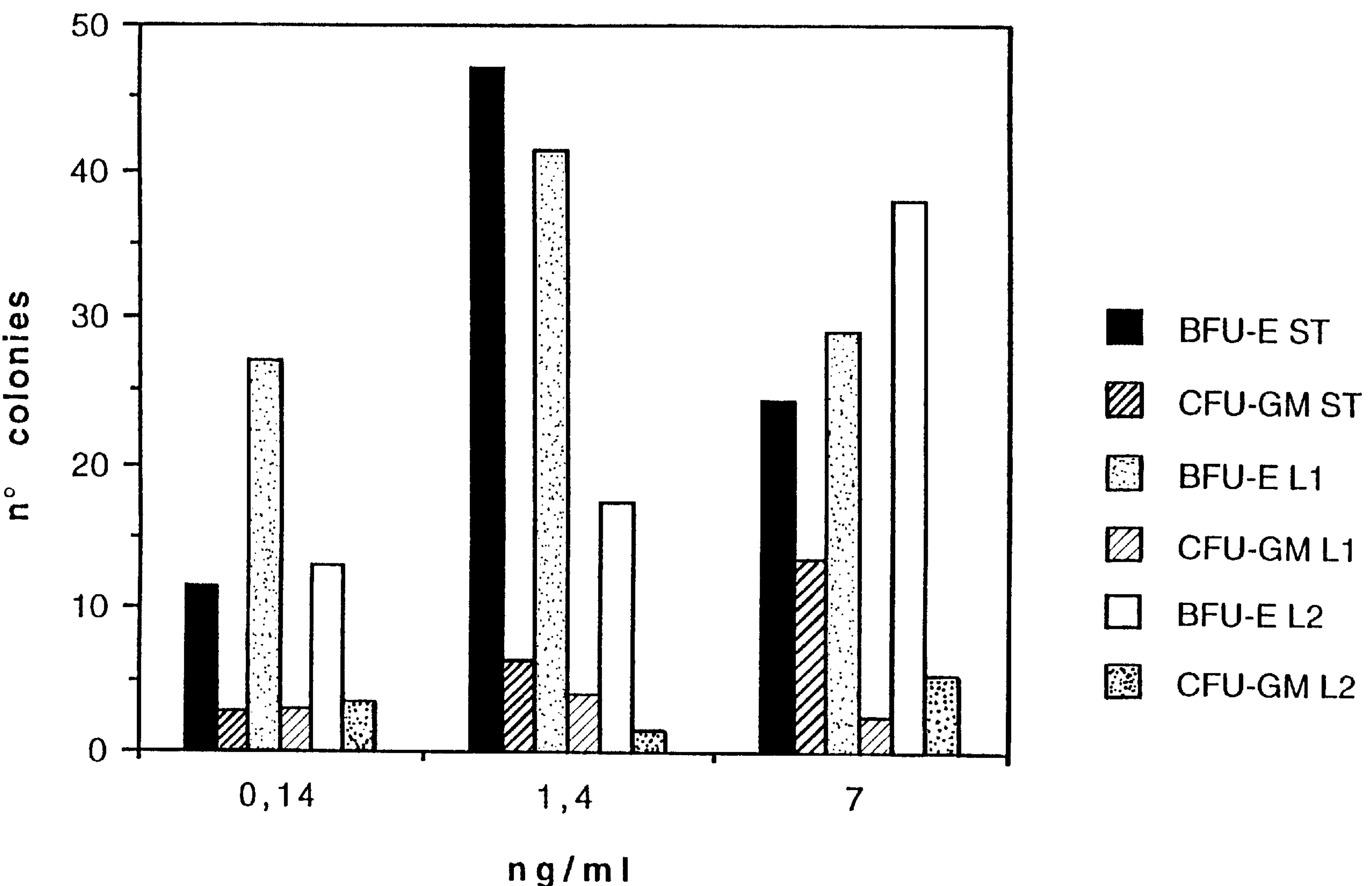
FIG. 5 shows a histogram wherein the concentration of growth factors added to the culture are expressed in ng/ml is reported in the abscissas, whereas the axis of ordinates reports the number of erythroid (BFU-E) and granulocyte-macrophage (CFU-GM) colonies induced by the mixture of the two growth factors GM-CSF and EPO (Standard) or by the hybrid molecules L1 and L2.

The results show that the GM-CSF and EPO factors linked as a single hybrid polypeptide chain induce, in the human stem cell cultures, a higher number of erythroid colonies and a lower number of granulocyte-macrophage colonies than the colonies treated with equimolar amounts of the mixture of the two factors not-linked (FIG. 5). These data show a higher specifity of action on the erythroid differentiation of the hybrid molecules compared to the same molecules not-linked.

Table 1 shows that the ratio between the number of erythroid and granulocyte-macrophage colonies results higher in the cultures treated with the hybrid molecules than in the cultures treated with equimolar amount of the two not-linked factors (GM-CSF and EPO Standard from Genetic Institute and Amgen, respectively). This fact was independent from the assayed concentrations (Table 1).

Further, another characteristic of the present invention is a process for the production of the hybrid protein according to the invention, comprising the cultivation of the host cell above described, according to the methods known in the art, under suitable conditions for the expression of the DNA sequence and the recovery of the protein from the culture.

Another characteristic of the present invention is also a pharmaceutical composition comprising the hybrid protein according to the invention, in combination with pharmaceutically suitable carriers or excipients.

Furthermore, the present invention also refers to the use of the hybrid protein according to the invention, for the preparation of a pharmaceutical composition useful for the erythropoiesis stimulation.

TABLE 1

| Amount | BFU-E/CFU-GM | | | |
|---|---|---|---|---|
| (ng/ml) | GM-CSF + EPO | L1* | L2** | L3*** |
| 0.14 | 1.4 | 3.0 | 2.25 | 1.4 |
| 1.4 | 4.6 | 9.0 | 6.7 | 5.0 |
| 7.0 | 7.2 | 10.0 | 11.6 | 8.0 |

*GM-CSF-L1-(Δ 1–4)EPO

**GM-CSF-L2-(Δ 1–4)EPO

***EPO-L3-GM-CSF

We claim:

1. A hybrid protein for the stimulation of hematopoiesis, having the formula

GM-CSF-L-EPO or

EPO-L-GM-CSF, wherein L is a peptide linker GM-CSF and EPO represent moieties having the amino acid sequences of GM-CSF or erythropoietin proteins or fragments thereof, respectively, provided that polypeptides having the amino acid sequences of said proteins or fragments retain the cell growth-and differentiation-promoting properties of native GM-CSF or erythropoietin.

2. A hybrid protein according to claim 1, wherein the linker consists of 5–50 amino acids.

3. A hybrid protein according to claim 2, wherein the linker comprises at least one of the sequences Gly-Gly-Gly-Gly-Ser (positions 2–6 of SEQ ID NO: 3) or Gly-Gly-Ala-Gly-Ser (positions 7–11 of SEQ ID NO: 3).

4. A hybrid protein according to claim 1, comprising from N-terminus to C-terminus the following components:

a) amino acids 1–127 of human GM-CSF;

b) the linker;

c) amino acids 5–166 of human erythropoietin.

5. A hybrid protein according to claim 1, comprising from N-terminus to C-terminus the following components:

a) amino acids 1–166 of human erythropoietin;

b) the linker;

c) amino acids 1–127 of human GM-CSF.

6. A hybrid protein according to claim 4, wherein said linker is a sequence of 16 amino acids.

7. A hybrid protein according to claim 6, wherein said linker is the sequence of SEQ ID NO:3 or the sequence of SEQ ID NO: 9.

8. A hybrid protein according to claim 4, wherein said linker is a sequence of 8 amino acids.

9. A hybrid protein according to claim 8, wherein said linker is the sequence of SEQ ID NO: 6.

10. A DNA molecule encoding a hybrid protein according to claim 1.

11. A DNA molecule according to claim 10, comprising from 5' to 3' the following components:

a) the untranslated 5' region of a human GM-CSF cDNA;

b) a sequence encoding the GM-CSF moiety;

c) an oligonucleotide encoding the linker;

d) a sequence encoding the EPO moiety;

e) the untranslated 3' region of a human erythropoietin cDNA.

12. A DNA molecule according to claim 10, comprising from 5' to 3' the following components:

e) the untranslated 5' region of a human erythropoietin cDNA;

b) a sequence encoding the EPO moiety;

c) an oligonucleotide encoding the linker;

d) a sequence encoding the GM-CSF moiety;

e) the untranslated 3' region of a human GM-CSF cDNA.

13. A DNA molecule according to claim 11, wherein said oligonucleotide is a sequence of 48 nucleotides.

14. A DNA molecule according to claim 13, wherein said oligonucleotide has the sequence of SEQ ID NO: 2.

15. A DNA molecule according to claim 13, wherein said oligonucleotide has the sequence of SEQ ID NO: 8.

16. A DNA molecule according to claim 11, wherein said oligonucleotide is a sequence of 24 nucleotides.

17. A DNA molecule according to claim 16, wherein said oligonucleotide has the sequence of SEQ ID NO: 5.

18. A recombinant expression vector comprising the sequence of a DNA molecule according to claim 10.

19. A host cell comprising a vector according to claim 18, wherein said host cell is a bacterial, yeast, insect, plant, or mammalian cell.

20. A process for producing a hybrid protein, comprising the steps of culturing a host cell according to claim 19 under conditions suitable for expression of the DNA encoding the hybrid protein, and recovering the protein from the culture.

21. A pharmaceutical composition comprising a hybrid protein according to claim 1, and one or more suitable carriers or excipients.

* * * * *